United States Patent [19]

Kim

[11] Patent Number: 5,430,900
[45] Date of Patent: Jul. 11, 1995

[54] BED EMITTING THE FAR INFRARED RAYS

[76] Inventor: Sung-Jul Kim, 601, Sung Chang villa, 426-285, Moon Hyon-dong, Nam-ku, Busan, Rep. of Korea

[21] Appl. No.: 147,475

[22] Filed: Nov. 4, 1993

[51] Int. Cl.⁶ .............................................. A61G 7/04
[52] U.S. Cl. ................................................ 5/421; 5/448; 5/459; 5/470; 5/284
[58] Field of Search .................... 5/284, 421, 448, 450, 5/459, 470; 126/261; 607/104, 96

[56] References Cited

U.S. PATENT DOCUMENTS

| | | | |
|---|---|---|---|
| 4,663,516 | 5/1987 | Blum | 5/421 X |
| 4,680,822 | 7/1987 | Fujino et al. | 5/448 X |
| 4,825,868 | 5/1989 | Susa et al. | 5/421 X |
| 5,146,633 | 9/1992 | Kim et al. | 5/421 |
| 5,259,379 | 11/1993 | Kim et al. | 5/421 X |

Primary Examiner—Michael F. Trettel
Attorney, Agent, or Firm—Jacobson, Price, Holman & Stern

[57] ABSTRACT

A bed comprising a base having an internal area into which a heat source, in the form of a hot water pipe system is installed, and mineral powder which together with the heat source, fills the internal area of the base and provides a top sleeping surface for the bed. When heated the bed emits far infrared rays which can be absorbed into the human body during sleep. It is thought that a bed of this type would have various therapeutic uses.

5 Claims, 3 Drawing Sheets

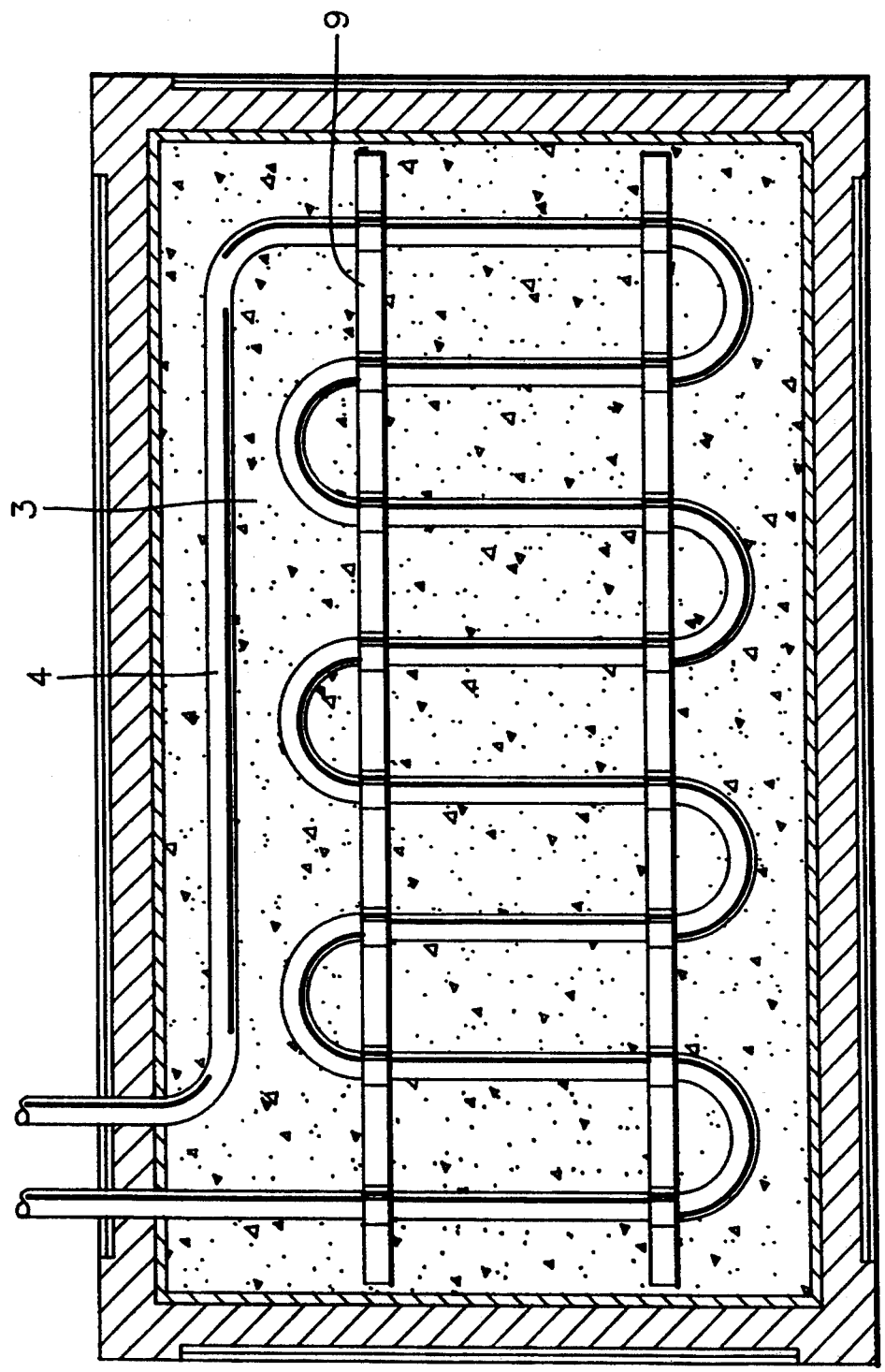

BED EMITTING THE FAR INFRARED RAYS

BACKGROUND OF THE INVENTION

1. Field of The Invention

This present invention relates to a bed emitting far infrared rays which can be absorbed into the human body during sleep. More specifically the present invention relates to a bed comprising a base having an internal area into which a heat source in the form of a hot water pipe system is installed within mineral powder which fills the internal area of the base and provides a top sleeping surface for the bed. It is envisaged that the surface would be covered and that such a cover would be a cloth material, fastened by means of at least one hook and loop (VELCRO) fastener or the like, in order to provide a cover that is removable as required.

2. Description of the Prior Art

The bed known in the art has a mattress filled with sponge and springs which is put into or on top of the base of the bed. This arrangement of the prior bed provides a good cushion effect, however, a bed of this type cannot protect the human body from the abnormal terrestrial magnetism which is emitted from cement walls or floors and the like and the electromagnetic waves from electronic machinery which are known to cause various types of sickness in humans, by depriving the human body of energy and physical strength and which also disturb a deep sleep.

SUMMARY OF THE INVENTION

It is an object of this invention to provide a bed that emits far infrared rays for absorption into the human body during sleep, by filling the bed, specifically the base of the bed with mineral powder, in combination with a heat source which emits far infrared rays instead of a mattress comprised of sponge and spring.

A further object of the present invention is to provide a fomentation effect as well as a heating effect by applying heat to the mineral powder via a heat source in the form of a hot water pipe system.

Another object of the present invention is to provide protection from the abnormal terrestrial magnetism and electromagnetic waves emanating from, for example cement walls or floors and to increase the vigor of the human body by neutralizing the alkalinity.

In the light spectrum, far infrared rays are located in the lower region, having the longest wavelength of the infrared rays. Being in a lower region than red visible rays when emitted, far infrared rays provide heat.

As a result of clinical demonstration, it has been shown that far infrared rays permeate into the human body by radiant and permeant force and improve the efficiency of movement of capillary vessels, which causes an increase in the circulation of the blood and activates molecular movement substances by consonance-absorption function. This affects the enzyme-group hormones and the substance of the physiological activation to promote systemic metabolism.

The present invention provides a bed that emits far infrared rays which can be absorbed into the human body during sleep, by filling the bed, specifically the base of the bed, with mineral powder and providing heat from a source within the mineral powder for emitting far infrared rays from the top surface of the bed.

In the present invention, by applying heat to the mineral powder through a heating source preferably in a form of a hot water pipe system, far infrared rays are emitted from a top surface of the bed so that a fomentation and heating effect is obtained.

BRIEF DESCRIPTION OF THE DRAWINGS

FIG. 3 is an internal plan view of a bed of the present invention.

DESCRIPTION OF THE INVENTION

Figure 1:
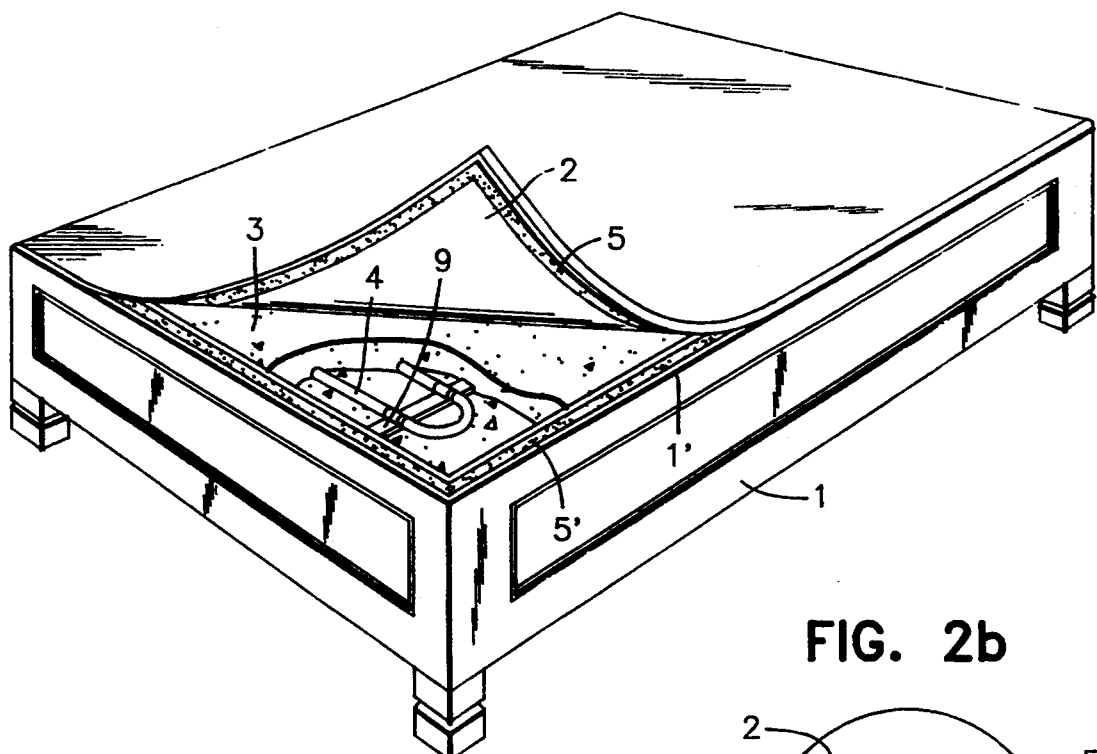
FIG. 1 is a perspective view of one embodiment of the present invention.
Figure 2B:
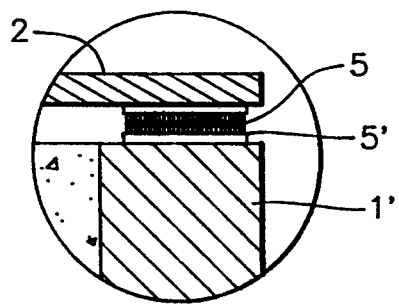
FIG. 2a is a cross-sectional view of a bed according to the present invention and FIG. 2b is an exploded view of attachment means.

The present invention will be described with respect to the drawings:

In FIG. 1, one aspect of the present invention is shown wherein mineral powder 3 fills the base 1 of the bed to provide a top sleeping surface 10 for the bed and in which a heat source in the form of a hot water pipe system 4 is installed. A cover 2 is provided over the top sleeping surface 10 and is secured using at least one hook (VELCRO) fastener 5, located around the basal edge of the cover 2 and at least one loop (VELCRO) fastener 5' located on the upper girth 1' of the base 1 of the bed, shown in FIG. 2b. The cover 2 can therefore be attached or detached for example when it is necessary to remove the cover from the bed.

Figure 2A:
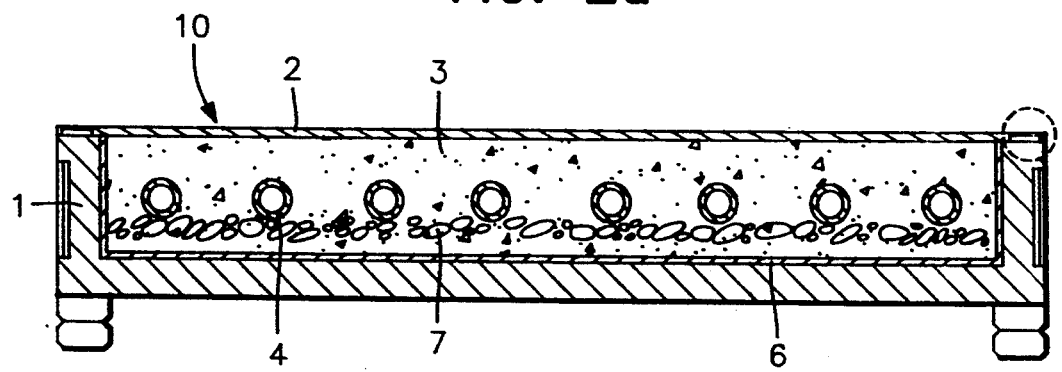

FIG. 2a shows the preferred internal construction and arrangement of a bed according to the present invention. A heat retardation layer or lagging material 6 provides a layer over the internal surface of the base 1 of the bed. This prevents the loss of heat through the base of the bed so that heat from the heat source is conducted through the mineral powder 3 for emission of far infrared rays from the top surface 10. As seen a hot water pipe system 4 is installed within the mineral powder 3, and is arranged uniformly throughout the mineral powder 3, to distribute the heat evenly as shown in FIG. 3. In particular, the hot water pipe system 4 would be located on the surface of a gravel layer 7 which is laid at the base of the mineral powder 3. The hot water pipe system 4 would be fixed within the base 1 by a securing plate 9, to prevent movement of the pipe system 4.

Figure 4:
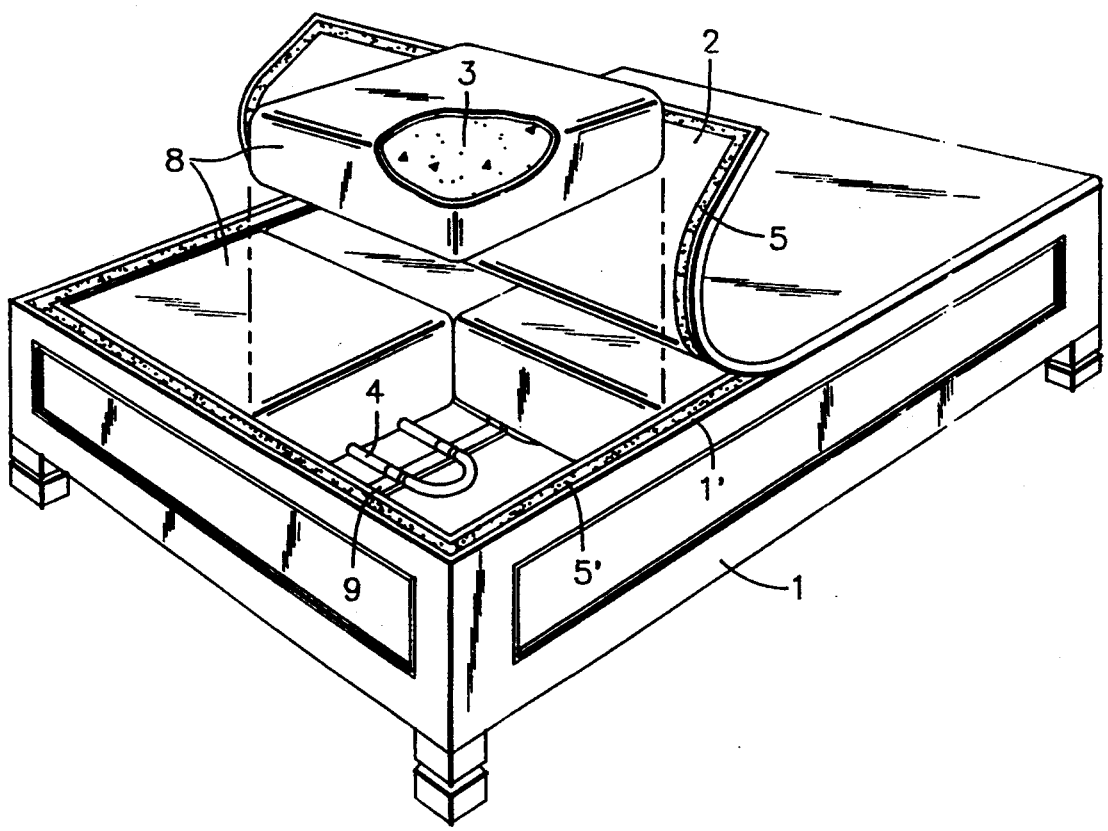
FIG. 4 is a perspective view of a further embodiment of the present invention.
Figure 5:
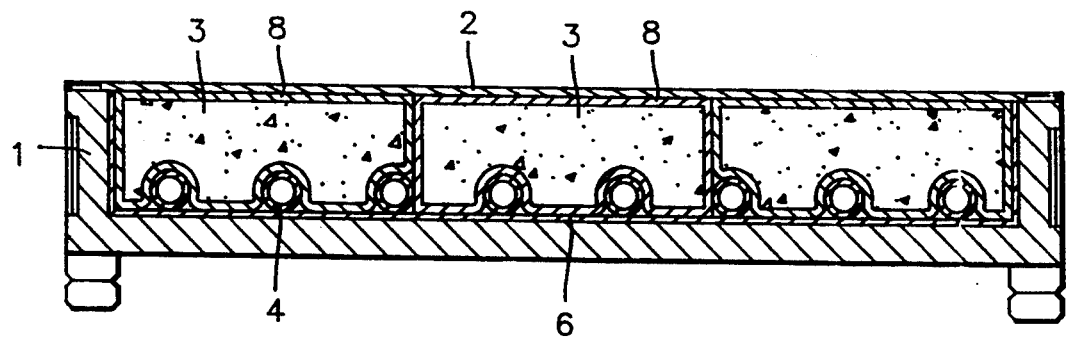
FIG. 5 is a cross-sectional view of FIG. 4.

FIGS. 4 and 5 show a further embodiment of the present invention wherein the mineral powder 3 is contained within several appropriately-sized bags 8, which are contained in the base 1 of the bed connectively and whose upper side is covered with the cover 2 secured by means of hook (VELCRO) fastener 5 and loop (VELCRO) fastener 5', so that it can be removed as needed.

In the present invention, it is envisaged that mineral powder 3 is made by crushing natural minerals and contains 26.67%, $Al_2O_3$, 0.1%, $F_2O_3$, 0.22%, $Na_2O$, 6.87%, $K_2O$, 64.67%, $SiO_2$, 0.61%, MaO and 0.02%, $TiO_2$, percentages given being "weight percentages". According to test results, the radiant intensity and rate of far infrared rays are more than 80% at a temperature of 40° C. in the zone of far infrared rays.

It is envisaged that mineral powder 3 would fill the base 1 of the bed, so that it would be level with the upper girth 1' of the bed. The internal area of the base 1 is covered with a heat retardation layer such as lagging material 6, and the hot water pipe system 4 is buried within the mineral powder 3, which fills the internal area of the base of the bed.

When hot water is supplied to the hot water pipe system 4, most likely, the hot water is heated by gas boiler or the like, and is circulated through the hot water pipe system 4 so that the mineral powder 3 is heated. In particular, since the hot water pipe system 4, which is supported by a securing plate 9, lies over the surface of the gravel layer 7 which provides a high heat conductivity, the time required to heat the mineral powder 3 is reduced.

Since the cover 2 can be attached and detached from the base 1 of the bed, it is easy to remove the cover 2 when it is necessary, for example, to wash the cover 2, level the surface of the mineral powder 3 or install or work on the hot water pipe system 4. Moving the bed, is easily achieved when necessary by taking off the cover 2, taking out the mineral powder 3, disconnecting the hot water pipes, moving the base 1 of the bed, refilling the base 1 of the bed with the mineral powder 3 and covering with the cover 2 so as to provide the sleeping surface 10. The cover is then secured to the bed by means of hook (VELCRO) fastener 5 and loop (VELCRO) fastener 5', although any type of non-permanent fastener would be considered.

FIGS. 4 and 5 illustrate a preferred embodiment of the present invention. Since mineral powder 3 is contained within appropriately-sized bags 8, installing or moving the bed is completed easily. For example the bags 8 are easy to assemble inside the base 1 of the bed and can be easily removed from the base 1.

If a person sleeps on the bed which contains the heated mineral powder 3, whereby the surface of the bed is covered with the cover 2, the far infrared rays emitted permeate the system and contact the human body directly.

In use the bed of the present invention activates the energy of the human body, speeds up molecular movement to promote metabolism, relieves stress and fatigue and provides a deep sleep. In particular the present invention in use prevents various kinds of sickness in humans by increasing the energy and physical strength of the human body through the fomentation effect.

I claim:

1. A bed for emitting far infrared rays comprising:
   a base having an internal space, said internal space lined with a heat lagging material;
   mineral powder filling the internal space, the mineral powder providing a top sleeping surface for the bed and comprising 26.67% by weight $Al_2O_3$, 0.1% by weight $F_2O_3$, 0.22% by weight $Na_2O$, 6.87% by weight $K_2O$, about 64.67% by weight $SiO_2$, 0.61% by weight MaO and 0.02% by weight $TiO_2$;
   a hot water pipe system fixably mounted within the internal space, substantially below the top surface of the bed, said hot water pipe system being arranged in a serpentine configuration, evenly throughout the mineral powder so that heat is conducted uniformly through the mineral powder and far infrared rays are emitted from the top sleeping surface of the bed;
   an external hot water supply connected to said hot water pipe system; and
   a fabric cover, at least for the top sleeping surface, having at least one hook and loop fastening means to secure the cover to the base of the bed.

2. The bed according to claim 1 further comprising a means within the internal space of the base of the bed to compartmentalize the mineral powder.

3. The bed according to claim 2 wherein said compartmentalizing means is in the form of at least one bag which contains the mineral powder.

4. The bed according to claim 3 wherein at least one bag is arranged on top of the hot water pipe system.

5. The bed according to claim 1 further comprising a gravel layer located substantially below the hot water pipe system.

* * * * *